United States Patent
Chen et al.

(10) Patent No.: US 12,102,516 B2
(45) Date of Patent: *Oct. 1, 2024

(54) PRODUCTS WITH MATERIALS THAT SHRINK IN ONE DIMENSION AND EXPAND IN ANOTHER DIMENSION

(71) Applicant: Kimberly-Clark Worldwide, Inc., Neenah, WI (US)

(72) Inventors: Jin Chen, Appleton, WI (US); Xuedong Song, Alpharetta, GA (US); William Clayton Bunyard, DePere, WI (US); Andrew M. Long, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 955 days.

This patent is subject to a terminal disclaimer.

(21) Appl. No.: 16/982,810

(22) PCT Filed: Mar. 22, 2018

(86) PCT No.: PCT/US2018/023708
§ 371 (c)(1),
(2) Date: Sep. 21, 2020

(87) PCT Pub. No.: WO2019/182594
PCT Pub. Date: Sep. 26, 2019

(65) Prior Publication Data
US 2021/0059876 A1 Mar. 4, 2021

(51) Int. Cl.
*A61F 13/537* (2006.01)
*A61F 13/15* (2006.01)
(Continued)

(52) U.S. Cl.
CPC ...... *A61F 13/537* (2013.01); *A61F 13/15577* (2013.01); *A61F 13/47* (2013.01);
(Continued)

(58) Field of Classification Search
CPC ................ A61F 13/15577; A61F 13/47; A61F 13/49007; A61F 13/53; A61F 13/537;
(Continued)

(56) References Cited

U.S. PATENT DOCUMENTS

| | | |
|---|---|---|
| 4,357,938 A | 11/1982 | Ito et al. |
| 4,447,240 A | 5/1984 | Ito et al. |

(Continued)

FOREIGN PATENT DOCUMENTS

| | | |
|---|---|---|
| CN | 1450885 A | 10/2003 |
| CN | 1476315 A | 2/2004 |

(Continued)

OTHER PUBLICATIONS

Omidian, H. et al., "Elastic, Superporous Hydrogel Hybrids of Polyacrylamide and Sodium Alginate," Macromolecular Bioscience, vol. 6, No. 9, 2006, pp. 703-710.

(Continued)

*Primary Examiner* — Michele Kidwell
(74) *Attorney, Agent, or Firm* — KIMBERLY-CLARK WORLDWIDE, INC.

(57) ABSTRACT

A disposable absorbent product includes a double-network polymer element including a cross-linked, covalently-bonded polymer and a reversible, partially ionicly-bonded polymer, wherein the element has a moisture level less than or equal to 15 percent of the total weight of the element, wherein the element comprises a latent retractive force, and wherein the element is configured to release the retractive force to achieve a dimensional change in the disposable absorbent product with exposure of the element to an aqueous liquid. Manufacturing a disposable absorbent product includes producing a double-network hydrogel; elongating by force and dehydrating while still elongated the double-network hydrogel, wherein elongating and dehydrat- (Continued)

ing captures a latent retractive force in the element; and positioning the element in a disposable absorbent product such that a dimensional change in the disposable absorbent product is achieved with exposure of the element to an aqueous liquid.

17 Claims, 10 Drawing Sheets

(51) Int. Cl.
  *A61F 13/47* (2006.01)
  *A61F 13/49* (2006.01)
  *A61L 15/26* (2006.01)
  *A61L 15/42* (2006.01)

(52) U.S. Cl.
  CPC ........ *A61F 13/49007* (2013.01); *A61L 15/26* (2013.01); *A61L 15/425* (2013.01); *A61F 2013/53773* (2013.01)

(58) Field of Classification Search
  CPC ......... A61F 2013/53773; A61L 15/225; A61L 15/26; A61L 15/42; A61L 15/425; C08L 33/26; C08L 5/04; C08L 77/12
  See application file for complete search history.

(56) References Cited

U.S. PATENT DOCUMENTS

| | | | |
|---|---|---|---|
| 4,942,089 | A | 7/1990 | Genba et al. |
| 5,210,117 | A | 5/1993 | Lee et al. |
| 5,932,495 | A | 8/1999 | Boney et al. |
| 6,030,634 | A | 2/2000 | Wu et al. |
| 6,271,278 | B1 | 8/2001 | Park et al. |
| 6,552,245 | B1 | 4/2003 | Roessler et al. |
| 6,605,349 | B2 | 8/2003 | Phillips |
| 6,627,673 | B2 | 9/2003 | Topolkaraev et al. |
| 6,960,617 | B2 | 11/2005 | Omidian et al. |
| 8,563,027 | B2 | 10/2013 | Jarrett et al. |
| 8,715,257 | B2 | 5/2014 | Dorschner |
| 8,821,583 | B2 | 9/2014 | Myung et al. |
| 8,828,434 | B2 | 9/2014 | Su et al. |
| 8,916,683 | B2 | 12/2014 | Olsen et al. |
| 10,486,136 | B2 * | 11/2019 | Song .................. B01J 20/28033 |
| 10,632,223 | B2 | 4/2020 | Song |
| 11,602,730 | B2 * | 3/2023 | Song ...................... C08L 33/26 |
| 2003/0018312 | A1 | 1/2003 | Pesce et al. |
| 2003/0049480 | A1 | 3/2003 | Gagliardini et al. |
| 2003/0068944 | A1 | 4/2003 | Carlucci et al. |
| 2004/0049166 | A1 | 3/2004 | Chen et al. |
| 2010/0174021 | A1 | 7/2010 | Huie, Jr. et al. |
| 2010/0198177 | A1 | 8/2010 | Yahiaoui et al. |
| 2010/0210752 | A1 | 8/2010 | Muratoglu et al. |
| 2010/0305526 | A1 | 12/2010 | Robinson et al. |
| 2012/0232502 | A1 | 9/2012 | Lowing |
| 2014/0296425 | A1 | 10/2014 | Tew et al. |
| 2015/0038613 | A1 | 2/2015 | Sun et al. |
| 2020/0030479 | A1 | 1/2020 | Song |

FOREIGN PATENT DOCUMENTS

| | | | |
|---|---|---|---|
| CN | 101161689 | A | 4/2008 |
| CN | 101608006 | B | 4/2011 |
| CN | 101891946 | B | 7/2012 |
| CN | 102226007 | B | 9/2012 |
| CN | 102827333 | A | 12/2012 |
| CN | 103396562 | A | 11/2013 |
| CN | 103923428 | A | 7/2014 |
| CN | 104497219 | A | 4/2015 |
| CN | 105175755 | A | 12/2015 |
| CN | 105461945 | A | 4/2016 |
| CN | 105696099 | A | 6/2016 |
| CN | 107236146 | A | 10/2017 |
| EP | 0804914 | A1 | 11/1997 |
| EP | 2026063 | A1 | 2/2009 |
| JP | 2005526879 | A | 9/2005 |
| JP | 2008542518 | A | 11/2008 |
| KR | 20020073553 | A | 9/2002 |
| KR | 20140120721 | A | 10/2014 |
| RU | 2207834 | C2 | 7/2003 |
| RU | 2298022 | C2 | 4/2007 |
| WO | 9800082 | A1 | 1/1998 |
| WO | 06132661 | A1 | 12/2006 |
| WO | 14169119 | A1 | 10/2014 |
| WO | 14176304 | A1 | 10/2014 |
| WO | 15013306 | A1 | 1/2015 |
| WO | 2017/058152 | * | 4/2017 ............. A61L 15/24 |
| WO | 17058152 | A1 | 4/2017 |

OTHER PUBLICATIONS

Sun, Jeong-Yun et al., "Highly Stretchable and Tough Hydrogels," Nature, Macmillan Publishers, vol. 489, Sep. 6, 2012, pp. 133-136.
Calo, Enrica and Vitaliy V. Khutoryanskiy, "Biomedical Applications of Hydrogels: A Review of Patents and Commercial Products," European Polymenr Journal, 65, 2015, pp. 252-267.
Wang, Jilong et al., 'Ion-linked double-network hydrogel with high toughness and stiffness,' Journal of Materials Science (2015)50:5458-5465.May 19, 2015).
Zhang, Huijuan et al., 'Thermal-responsive poly(N-isopropyl acrylamide)/sodium alginate hydrogel: preparation, swelling behaviors, and mechanical properties,' Colloid Polym Sci (2016) 294:1959-1967, published online on Oct. 12, 2016.
Zhang et al., A free-standing calcium alginate/polyacrylamide hydrogel nanofiltration membrane with high anti-fouling performance: prepartion and characterization, Desalination, 2015, pp. 234-241.

* cited by examiner

PRODUCTS WITH MATERIALS THAT SHRINK IN ONE DIMENSION AND EXPAND IN ANOTHER DIMENSION

BACKGROUND

The present disclosure is generally directed to disposable absorbent products using absorbent and shrinkable materials. In particular, the present disclosure is directed to materials that shrink in one dimension and expand in another dimension when absorbing a liquid such as water or a bodily fluid.

Responsive materials that can potentially address many unmet consumer needs associated with existing products are needed. New applications of those responsive materials can also stimulate exploration and development of emerging products beyond current categories.

Related materials can include water-shrinkable fibers; however, they are not hydrogels, they do not shrink to the same magnitude, and they do not possess elastic properties. Previous attempts at producing responsive materials include materials such as those described in U.S. Pat. No. 4,942,089 to Genba et al. related to shrinking fiber, water-absorbing shrinkable yarn, and other similar materials. Shrinking fibers that are hardly soluble in water and that are capable of shrinking in water at 20° C. by not less than 30% in not longer than 10 seconds are obtained, for example, by spinning, drawing, and heat-treating a carboxy-modified polyvinyl alcohol under specific conditions. Yarns made from a fiber of this kind in conjunction with nonwoven fabrics made by incorporating yarns containing such shrinking fibers in nonwoven fabrics that are shrinkable upon absorption of water have been proposed for tightly fitting edge portions of disposable diapers to the thigh.

Conforming fit has been a long-standing challenge for personal care products including diapers, pull-ups, youth-pants, feminine pads, tampons, incontinence pads, and adult garments. Fit problems reside in four major categories: 1) current products do not fit well on all body types and for growth within the size; 2) current products are not in complete contact, or with enough contact pressure, in certain body areas during dynamic movement, positional change, and difficult body positions; 3) current products do not stay in place during dynamic movement (e.g., shifting downwardly during movement) or with certain body shapes (e.g., sliding lower in front if the wearer has a belly); and 4) current products do not maintain their primary shape after insult (e.g., quick swelling with small loadings, front drooping, bunching/twisting/drooping in crotch area).

In addition, fluid management has also been a long-standing challenge for such personal care products. One of the design challenges, for example, is to ensure enough effective bucket volume in a diaper to hold and contain liquid until it is absorbed, without any leakage. The present disclosure describes an innovative approach to create controllable, dynamic surface topography for efficient fluid management.

Although capable of absorbing fluids, conventional hydrogels are generally soft and fragile in a hydrated state and brittle and hard in a dried or dehydrated state. Conventional hydrogels have poor mechanical properties with poor stretchability and notch-resistance.

In addition, U.S. Patent Application Publication Number 2015/038613 to Sun et al. describes a hydrogel composition, but does not disclose drying/dehydrating such a composition under stress. PCT Patent Application Publication Number WO06132661 to Muratoglu et al. describes a hydrogel that is made "tougher" by dehydrating the hydrogel after "deforming" the hydrogel using compressive force.

As a result, there is a need to enable production of a disposable absorbent product with the attributes described herein.

SUMMARY

Unmet needs for existing products include conformance, comfort, and the reduction of leakage. Disclosed herein is a new type of responsive materials in different forms that can simultaneously shrink in one dimension and expand in one or more other dimensions upon contact with aqueous media and body fluids to form hydrogel materials. The materials also have significant absorbing capacity for water and other aqueous liquids. The materials are flexible.

Recently a new class of hydrogels, double-networked hydrogels, has been developed with very interesting mechanical properties such as high elasticity, toughness, and notch-resistance in hydrated state. Those materials can be used to address unmet needs in many different fields.

This approach is novel in the personal care product category in that it leverages stimuli-responsive shape-change materials for smart response of products. This approach addresses key fit problems and delivers fundamental knowledge for technical and perceptual fit. The surface topography and other dimensional changes created on demand serve the functional benefits of holding fluid at a target zone, managing fluid distribution, and minimizing skin fluid contact. As a result, faster intake, less leakage, and skin health benefits are achieved through incorporation of the technology.

A wet-triggered shrinkable material is described in co-pending U.S. patent application Ser. Nos. 15/561,595 and 15/564,766, which describe a type of double-network hydrogel materials that are wet-triggered, shrink remarkably, and become elastic after hydrated. For the present disclosure, such double-network hydrogel materials are incorporated into disposable absorbent products to create surface topography, pockets, and other dimensional changes through the wet-activated shape change of the material for better body fit and fluid containment.

In one aspect, a disposable absorbent product includes a double-network polymer element including a cross-linked, covalently-bonded polymer and a reversible, partially ionicly-bonded polymer, wherein the element has a moisture level less than or equal to 15 percent of the total weight of the element, wherein the element comprises a latent retractive force, and wherein the element is configured to release the retractive force to achieve a dimensional change in the disposable absorbent product with exposure of the element to an aqueous liquid.

In an alternate aspect, a disposable absorbent product includes a double-network polymer element including a cross-linked, covalently-bonded polymer and a reversible, partially ionicly-bonded polymer, wherein the element has a moisture level less than or equal to 15 percent of the total weight of the element, wherein the element comprises a latent retractive force, wherein the element is configured to release the retractive force to achieve a dimensional change in the disposable absorbent product with exposure of the element to an aqueous liquid, and wherein the release of the retractive force results in the element shrinking in at least one dimension and expanding in at least one dimension that is different from the shrinking dimension.

In another aspect, a method for manufacturing a disposable absorbent product includes producing a double-network hydrogel including a cross-linked, covalently-bonded polymer and a reversible, ionicly-bonded polymer; elongating by force the double-network hydrogel in at least one direction; dehydrating while still elongated the double-network hydrogel to form a substantially-dehydrated double-network polymer element; releasing the force to produce the element, wherein elongating and dehydrating captures a latent retractive force in the element; and positioning the element in a disposable absorbent product such that a dimensional change in the disposable absorbent product is achieved with exposure of the element to an aqueous liquid.

Objects and advantages of the disclosure are set forth below in the following description, or can be learned through practice of the disclosure.

BRIEF DESCRIPTION OF THE FIGURES

A full and enabling disclosure of the present disclosure, including the best mode thereof to one of ordinary skill in the art, is set forth more particularly in the specification, including reference to the accompanying figures in which.

Figure 1:
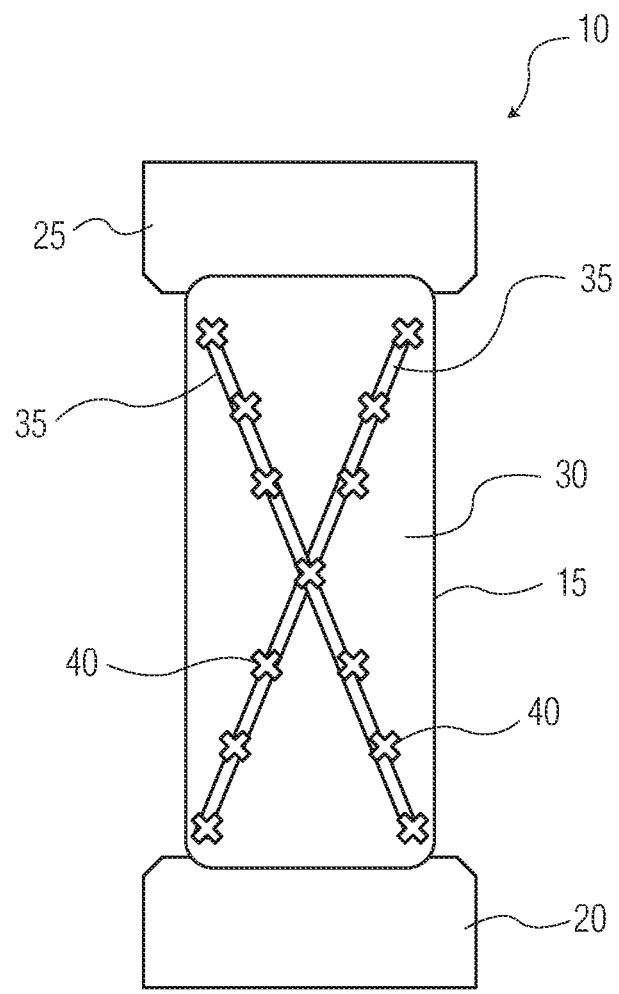
FIG. 1 is a plan schematic view of a disposable absorbent product in the form of a diaper with double-network polymer elements of the present disclosure.

Repeated use of reference characters in the present specification and drawings is intended to represent the same or analogous features or elements of the present disclosure.

DETAILED DESCRIPTION

As used herein the term "nonwoven fabric or web" refers to a web having a structure of individual fibers or threads that are interlaid, but not in an identifiable manner as in a knitted fabric. Nonwoven fabrics or webs have been formed from many processes such as for example, meltblowing processes, spunbonding processes, bonded carded web processes, etc.

As used herein, the terms "elastomeric" and "elastic" are used interchangeably and shall mean a layer, material, laminate or composite that is generally capable of recovering its shape after deformation when the deforming force is removed. Specifically, when used herein, "elastic" or "elastomeric" is meant to be that property of any material that, upon application of a biasing force, permits the material to be stretchable to a stretched biased length that is at least about fifty (50) percent greater than its relaxed unbiased length, and that will cause the material to recover at least forty (40) percent of its elongation upon release of the stretching force. A hypothetical example that would satisfy this definition of an elastomeric material would be a one (1) inch sample of a material that is elongatable to at least 1.50 inches and that, upon being elongated to 1.50 inches and released, will recover to a length of less than 1.30 inches. Many elastic materials can be stretched by much more than fifty (50) percent of their relaxed length, and many of these will recover to substantially their original relaxed length upon release of the stretching force.

Reference now will be made in detail to various aspects of the disclosure, one or more examples of which are set forth below. Each example is provided by way of explanation, not of limitation of the disclosure. In fact, it will be apparent to those skilled in the art that various modifications and variations can be made in the present disclosure without departing from the scope or spirit of the disclosure. For instance, features illustrated or described as part of one aspect, can be used on another aspect to yield a still further aspect. Thus it is intended that the present disclosure cover such modifications and variations.

This disclosure describes a modification of a double-network hydrogel. A double-network hydrogel is a hydrogel that includes two types of polymers. In this case, one is a cross-linked/covalently-bonded polymer; the second is a reversible/ionicly-bonded polymer. Double-network hydrogels have been reported to have superior mechanical properties such as strength, elasticity, and notch-resistance.

The double-network hydrogel of this disclosure is modified by stretching/stressing the double-network hydrogel while it is wet and then, while maintaining such stretching, drying it to lower than about a 10-15% moisture level. The resultant product material, a double-network polymer element that is not a hydrogel, remains strong and flexible when dry, but is not elastic. The cross-linked polymer of the double-network polymer element provides strength, whereas the ionicly-bonded polymer has had some of its bonds broken. Without being limited with respect to theory, it is believed that breaking these bonds during drying creates stored energy in the form of a latent retractive force in the dry double-network polymer element.

In a typical hydrogel, re-hydration leads to expansion in all three dimensions. Again, without being limited with respect to theory, it is believed that when the dry double-network polymer element of this disclosure is re-hydrated, some of the broken ionic bonds are re-formed. The double-network polymer element shrinks in one dimension (e.g., in the x-y plane), while it expands in another dimension (e.g., the z-direction, where the z-direction is perpendicular to the x-y plane). For example, a string-like sample of dry double-network polymer element demonstrated shrinkage in length from about 5 inches to 1 inch when re-hydrated, while the sample also expanded in diameter. A disk-shaped sample of the dry double-network polymer element shrank in diameter but increased in thickness.

Previous attempts to make wet-triggered shrinkable materials that become elastic after being hydrated used processes that are relatively cumbersome. Moreover, in general, the materials will not start to shrink until a couple of minutes after wetting when all the dimensions of the materials are more than 100 micrometers. In some cases, this time scale might not be a problem. The response speed, however, might not be fast enough in other cases such as tightening of gaps to prevent leakage in absorbent articles. An improved version of wet-triggered shrinkable materials is disclosed herein, where the materials include a large number of micro- and nano-pores in the wet-triggered shrinkable materials that become elastic upon hydration. In addition, a simplified process of making nonporous and porous wet-triggered shrinkable materials is also disclosed. The porous wet-triggered shrinkable materials include double-networked polymers and start to shrink and complete the shrinking process much faster than non-porous counterparts of the same dimension and general material description.

Conventional hydrogels are generally soft and fragile in their hydrated state and brittle and hard in a dried state. Conventional hydrogels have poor mechanical properties along with poor stretchability and notch-resistance. Recently a new class of hydrogels, double-networked hydrogels, has been developed with very interesting mechanical properties such as high elasticity, toughness, and notch-resistance when in a hydrated state. In this disclosure, porous wet-triggered shrinkable double-networked hydrogel materials are disclosed that respond to wetting much faster than nonporous counterparts. In addition, a simplified process has been developed to make the porous shrinkable materials.

In various aspects of the disclosure, a string, strand, sheet, or a fiber in a dry state (with less than 10-15% water content) contains a large number of pores. The pores can be in various sizes from micrometers to nanometers. The pores can be open or closed, although open pores are preferred.

This double-network polymer element can absorb many times its weight in water. Examples are detailed below in this disclosure.

In one specific aspect of the present disclosure, a material is made from at least one cross-linked hydrogel-forming polymer and at least a second hydrogel-forming polymer with reversible cross-linkers in which a significant portion of the cross-linkers (e.g., 30%) are not fully cross-linked and are in a free or partially-free state with the polymer in a dry state.

The cross-linked polymer can be polyacrylamide, polyacrylic acid, any other suitable polymer, or any combination of these. The reversible cross-linker can be alginate with sodium ions, gelatin with aluminum ions, any other suitable polymer, or any combination of these. In a dry state, sodium ions are not significantly cross-linked with alginate.

Previously-reported processes to make the base materials include the use of ultraviolet (UV) light for polymerization, cross-linking, and curing after mixing all the components in a container. This process sometimes produces materials that are fragile and are easy to tear. Presumably, UV light can damage some of the materials during polymerization and curing process. The improved process employed herein uses self-generated heat to accelerate polymerization and curing for making the materials without using UV light irradiation. The materials produced using this improved process are more consistent in terms of strength and shrinking performance. By placing all the ingredients under vacuum to remove oxygen, polymerization starts to generate heat that helps to accelerate polymerization, cross-linking, and curing. Unlike the previously-used process, this improved process does not need an extended period of curing to obtain sufficiently-performing materials.

This new disclosure is an improved version that contains a large number of micro- and nano-pores. This new version starts to shrink much faster (example starts to shrink 8 times faster) and completes the shrinking process much faster (example finishes shrinking 3 times faster).

As described further in the examples below, the present disclosure includes manufacturing the double-networked polymer elements. First, the double-networked hydrogels are manufactured in a hydrated state consistent with reported literature. The double-network hydrogels can be manufactured in a string, a sheet, or in any other suitable form. After curing the double-network hydrogels, the double-network hydrogels are stretched or elongated in one or two selected dimensions mechanically and dried while elongated. When the elongation force is released, the dried materials (double-network polymer elements) keep the dimensions they acquired under elongation without significant changes for a long period of time under ambient conditions.

While not shown, it can be desirable to use finishing steps and/or post treatment processes to impart selected properties to the dry double-network polymer element. For example, chemical post treatments can be added to the double-network polymer element at a later step, or the double-network polymer element can be transported to cutters, slitters, or other processing equipment for converting the double-network polymer element into a final product. Further, patterning can be placed through known processes into the outer surfaces of the double-network polymer element. The double-network polymer element can be in the form of fibers, a web, a string, a disk, a sheet, a solid prism, or any other suitable shape.

For the purposes of this disclosure, samples of double-network hydrogels were made using polyacrylamide as the cross-linked polymer and sodium alginate as the ionicly-bonded polymer. Additional detail with respect to the preparation and performance of such double-network hydrogels can be found in U.S. Patent Application Publication Number 2015/038613 to Sun et al., which is incorporated herein by reference to the extent it does not conflict herewith.

Potential applications of the double-network polymer element include embedding the dry double-network polymer elements in personal care products, absorbent medical products, and wipers in various string lengths or shapes. The dry double-network polymer element in a product will change shape or tighten when wetted, potentially leading to a change in shape or appearance of such products.

The positions of the embedded porous materials can vary depending upon the specific needs. The embedding methods can vary as well. Specific embedding methods include adhesives-based, ultrasound-based, hot-melting-based or mechanical bonding techniques such as sewing or needle-punching. Examples of the absorbent articles include diapers, training pants, feminine pads and liners, and incontinence garments.

In various aspects of the disclosure, a string/strand, or a sheet, or a fiber in a dry state (with less than or equal to 10-15% water content) shrinks in at least one dimension and expands in at least one other dimension upon contact with aqueous media. In addition, the strings/strands, sheets, or fibers absorb at least four times their weight in water. For instance, in the case of a string made from the double-network polymer element, the string's length becomes much shorter when wetted than it was in the original dry state when no external force is applied, whereas the diameter of the string becomes larger at the same time upon wetting. In another example, a sheet made from the double-network polymer element can shrink in length and width upon wetting or hydrating while its thickness increases at the same time.

A first example product application is schematically illustrated in FIG. 1. A diaper 10 generally includes a chassis 15, a front panel 20, and a back panel 25. The chassis 15 includes an absorbent core (internal, not shown) and a liner material 30. In this aspect, the chassis 15 also includes one or more double-network polymer elements 35 in the form of a bundle of fibers made from the double-network polymer. The double-network polymer elements 35 are selectively placed into the center of the chassis 15 as an X shape. The double-network polymer elements 35 can be anchored 40 to the liner 30 as illustrated in FIG. 1 or to another material in the diaper 10. The anchors 40 are shown as X shapes for illustrative purposes and can be any suitable shape in an actual diaper.

Figure 2:
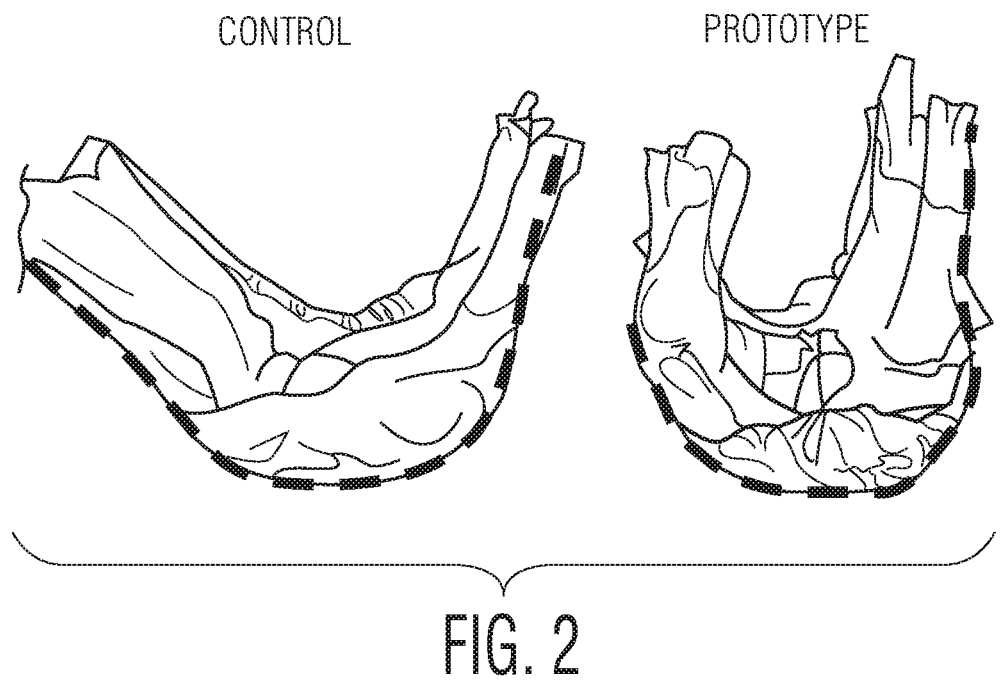
FIG. 2 is an elevation representation of a control diaper versus the prototype diaper of FIG. 1, both after insult, with the outer profile of the diapers emphasized with dashed lines.
Figure 3:
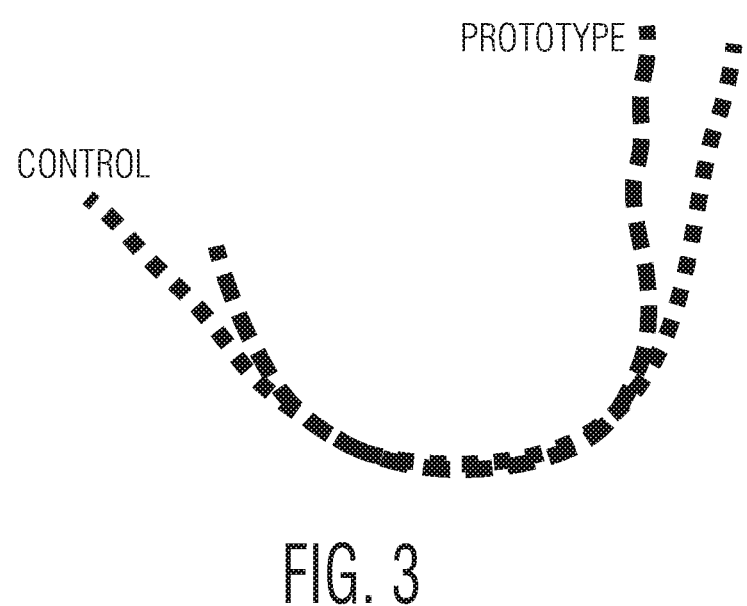
FIG. 3 is a graphical illustration of the outer profiles of the control and prototype diapers of FIG. 2, both after insult.

FIGS. 2 and 3 illustrate the performance of such a prototype diaper versus a control diaper with no double-network polymer elements. Upon wetting, in this case with three applications of 60 mL of saline for a total of 180 mL of saline, the double-network polymer elements in the prototype diaper shrink, creating a dimensional change not observed in the control diaper. FIG. 3 illustrates the outer curves of the prototype and controls diapers after insult, showing the greater shaping in the case of the prototype diaper, meaning the prototype diaper contours better to body shape. The prototype diaper also results in reduced sagging because the shrinking fiber counteracts the downward forces of the insulted absorbent core, holding the insulted absorbent core and the diaper itself snugly against the body. The shape change of the diaper was completed in 2 minutes.

Figure 4:
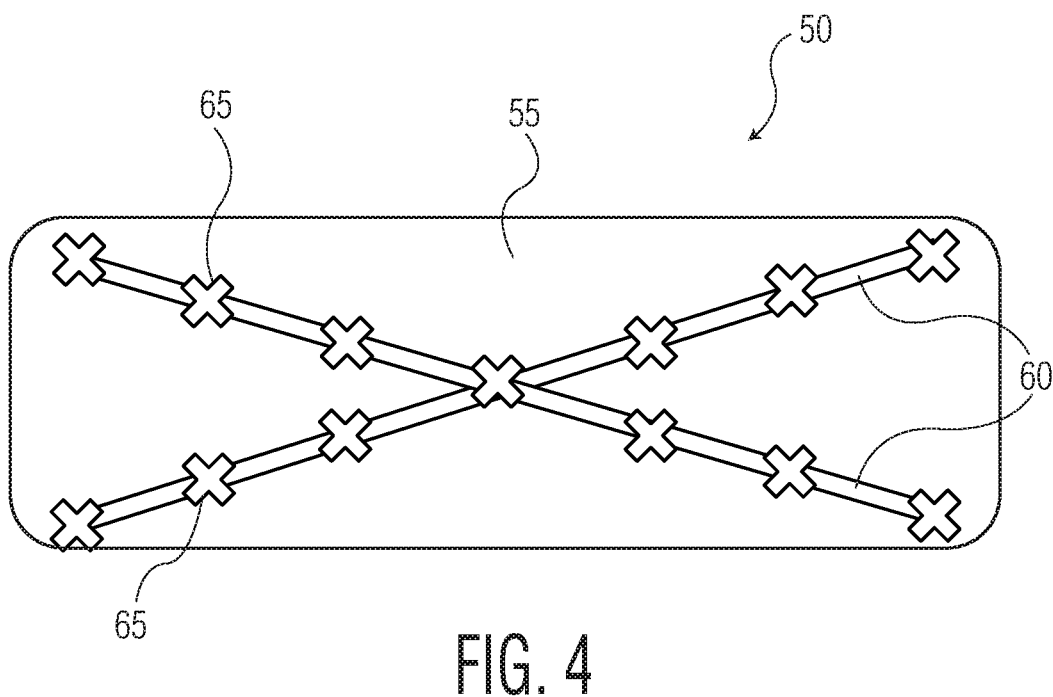
FIG. 4 is a plan schematic view of a disposable absorbent product in the form of a feminine pad with double-network polymer elements of the present disclosure.

In another example product application schematically illustrated in FIG. 4, a feminine pad 50 includes an absorbent core (internal, not shown) and a liner 55. The feminine pad 50 also includes one or more double-network polymer elements 60 in the form of a bundle of fibers made from the double-network polymer. The double-network polymer elements 60 are selectively placed into the center of the feminine pad 50 as an X shape. The double-network polymer elements 60 can be anchored 65 to the liner 55 as illustrated in FIG. 4 or to another material in the feminine pad 50. The anchors 65 are shown as X shapes for illustrative purposes and can be any suitable shape in an actual feminine pad.

Figure 5:
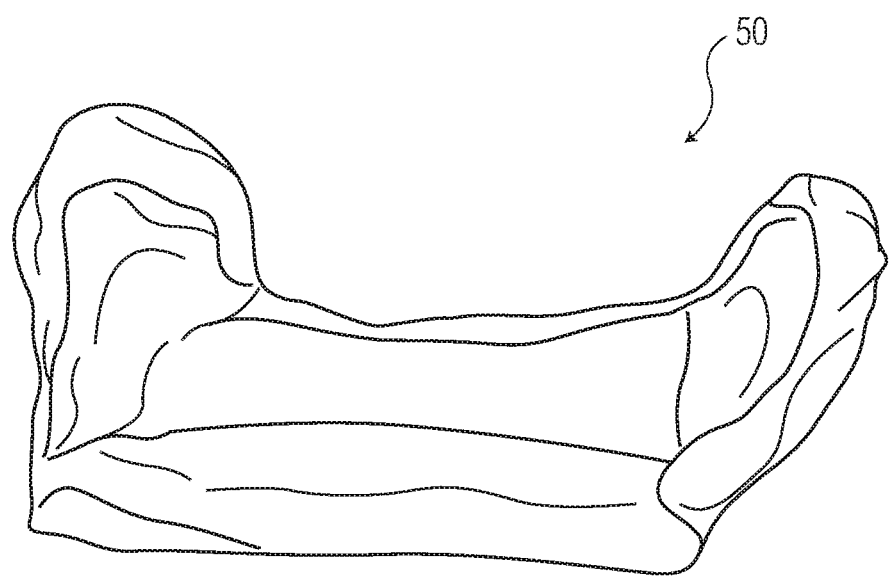
FIG. 5 is a perspective representation of the prototype feminine pad of FIG. 4, after insult.

FIG. 5 illustrates the performance of such a prototype feminine pad. Upon wetting with saline to simulate urine, the double-network polymer elements in the prototype feminine pad shrink, creating a dimensional change in which the ends of the pad lift to form a U shape. The resultant curved pad shape contours better to body shape. The shape change of the feminine pad completed in 45 seconds.

Figure 6:
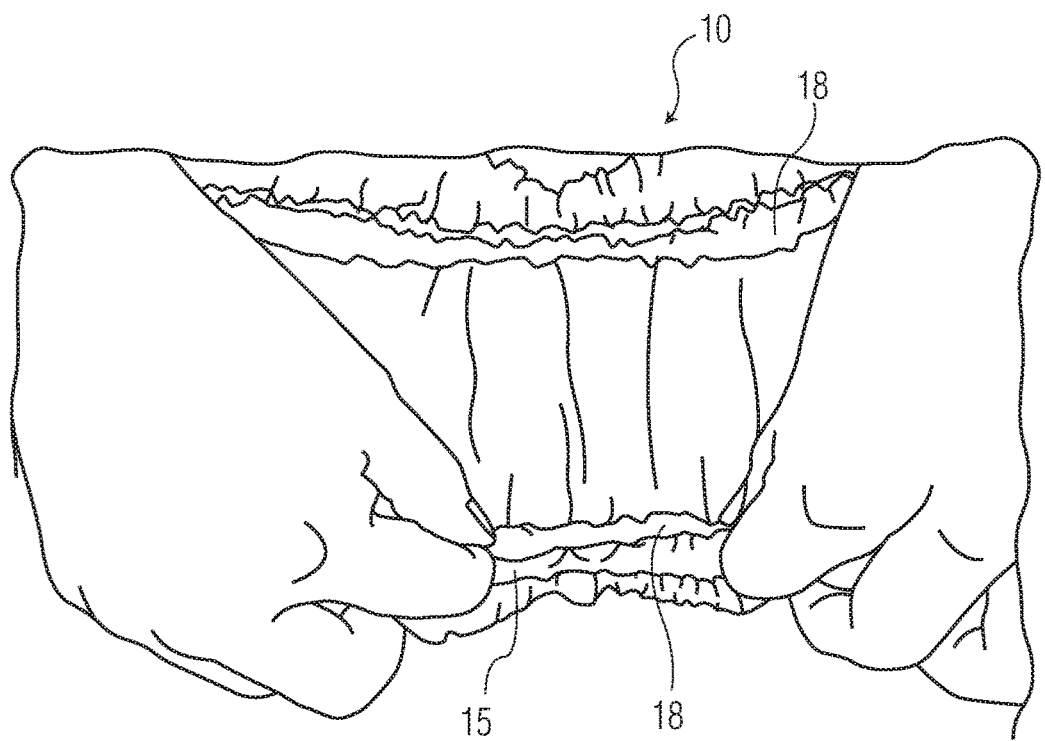
FIG. 6 is a plan representation of a prototype diaper with double-network polymer elements within secondary flaps, one of which is held be human hands for perspective.

In still another example product application schematically illustrated in FIG. 6, a diaper 10 includes a pair of secondary flaps 18 attached to the chassis 15. In this aspect, each secondary flap 18 includes one or more double-network polymer elements in the form of a bundle of fibers made from the double-network polymer built into the flaps 18. In a pre-insult condition, the secondary flap 18 remains flat against the chassis 15. Upon wetting with saline to simulate urine, the double-network polymer elements in the secondary flap 18 shrink, creating a dimensional change. The dimensional change results in the flap 18 standing up to maintain closer contact with the wearer's body. The resulting standing secondary flap 18 is also elastic.

Figure 7:
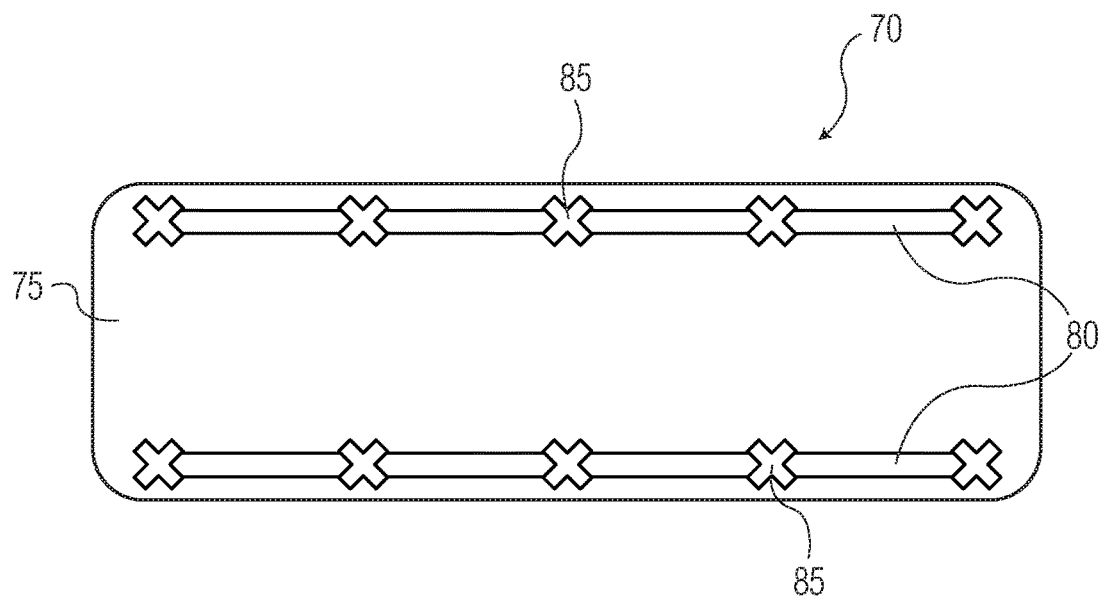
FIG. 7 is a plan schematic view of a disposable absorbent product in the form of a feminine pad with double-network polymer elements of the present disclosure.

In a fourth example product application schematically illustrated in FIG. 7, a feminine pad 70 includes an absorbent core (internal, not shown) and a liner 75. The feminine pad 70 also includes one or more double-network polymer elements 80 in the form of a bundle of fibers made from the double-network polymer. The double-network polymer elements 80 are selectively placed along the longitudinal edges of the feminine pad 70, and are encased in a nonwoven to create a flat flap 78. The double-network polymer elements 80 with their nonwoven casings can be anchored 85 to the liner 75 as illustrated in FIG. 7 or to another material in the feminine pad 70. The anchors 85 are shown as X shapes for illustrative purposes and can be any suitable shape in an actual feminine pad.

Figure 8:
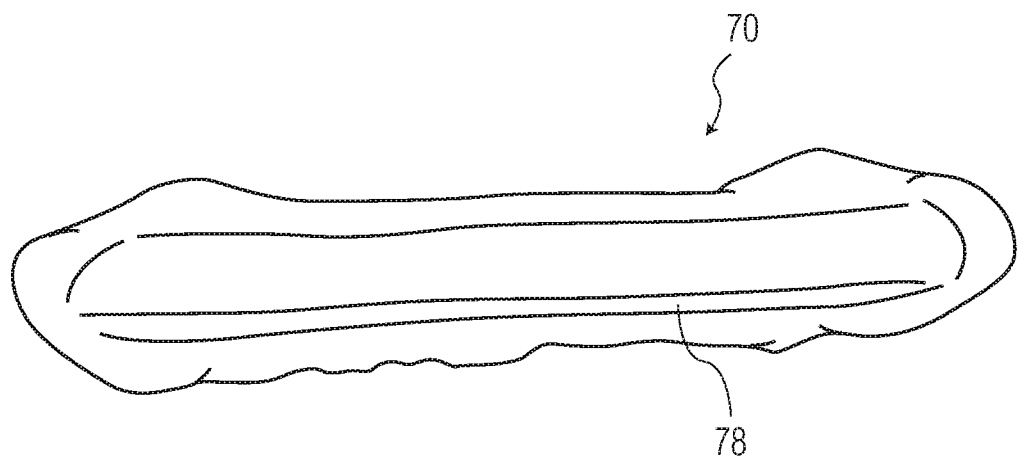
FIG. 8 is a perspective representation of the prototype feminine pad of FIG. 7, prior to insult.
Figure 9:
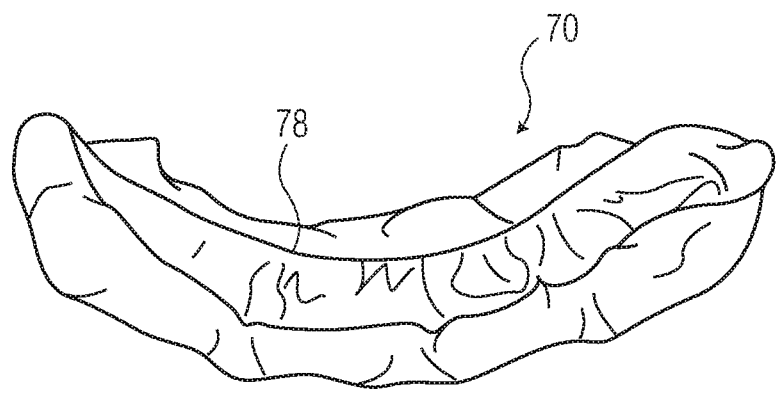
FIG. 9 is a perspective representation of the prototype feminine pad of FIG. 7, after insult.

FIGS. 8 and 9 illustrate the performance of such a prototype feminine pad 70. Prior to insult, the feminine pad 70 is flat (FIG. 8). Upon wetting with saline to simulate urine, the double-network polymer elements in the prototype feminine pad 70 shrink, creating a dimensional change (FIG. 9). The resultant curved pad shape and standing flaps 78 both contour better to body shape and better maintain contact with the body of the wearer. The resulting flap 78 is as elastic as conventional elastic material. This prototype also works similarly with menses simulant.

Figure 10:
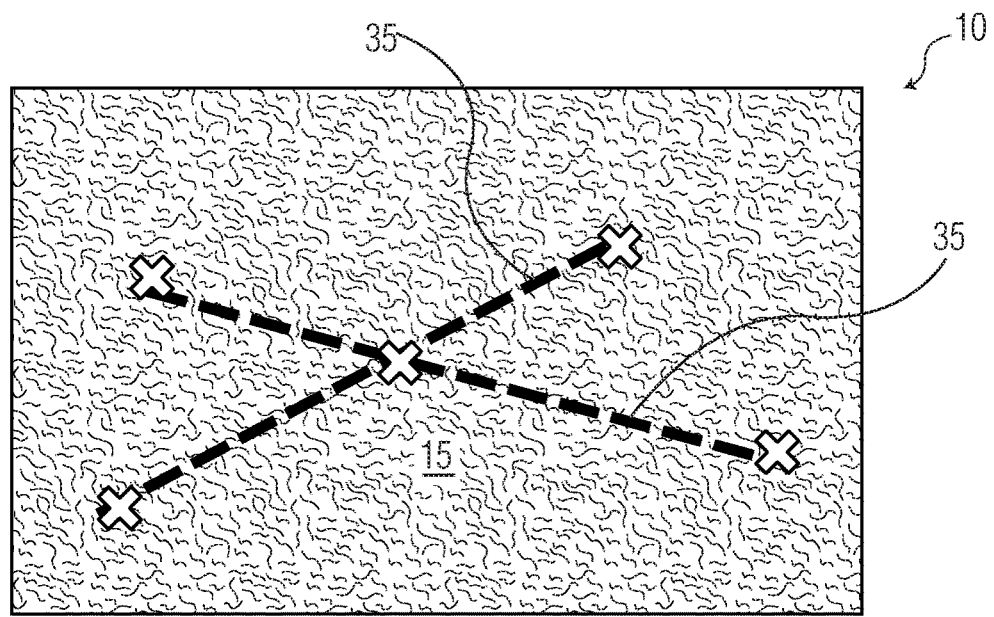
FIG. 10 is a plan schematic illustration of a portion of a prototype diaper with double-network polymer elements of the present disclosure, prior to insult.
Figure 11:
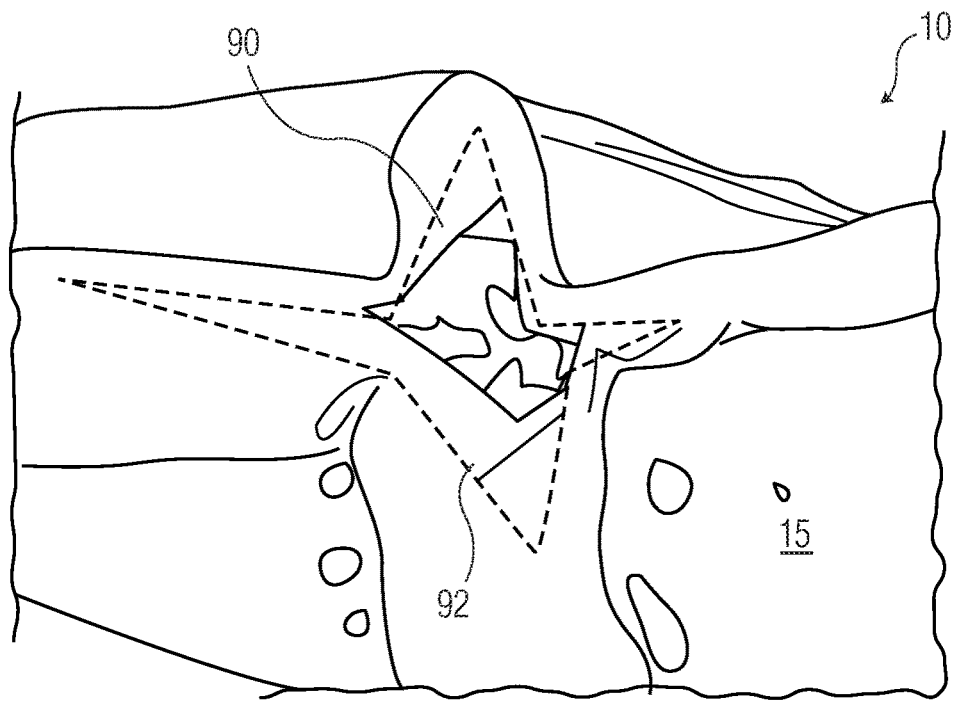
FIG. 11 is a plan schematic illustration of the prototype diaper portion of FIG. 10 with double-network polymer elements, after insult.
Figure 12:
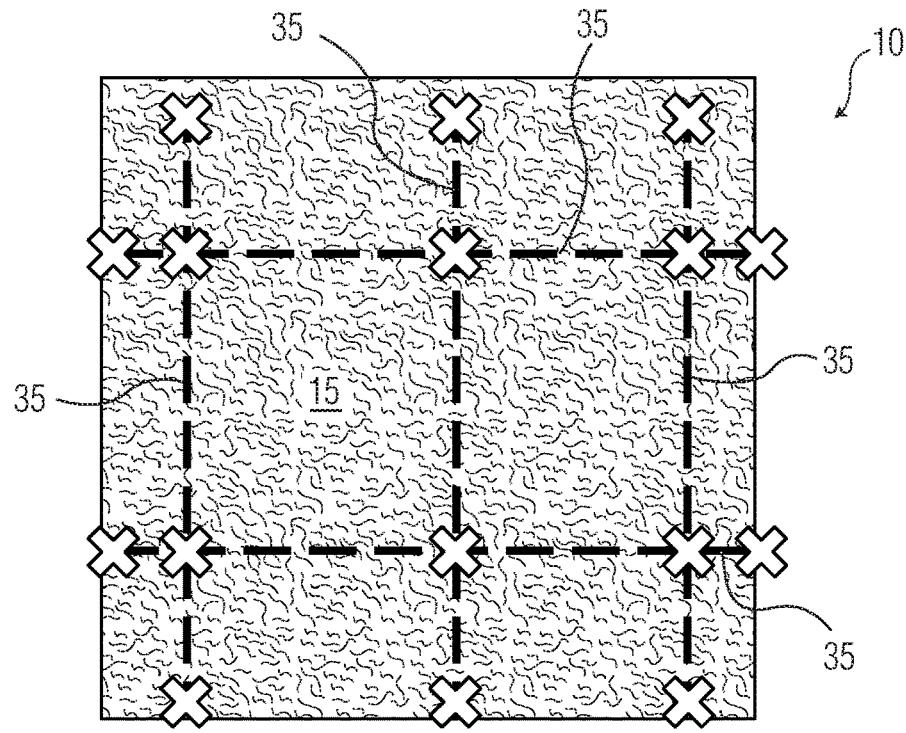
FIG. 12 is a plan schematic illustration of a portion of a prototype diaper with double-network polymer elements of the present disclosure, prior to insult.
Figure 13:
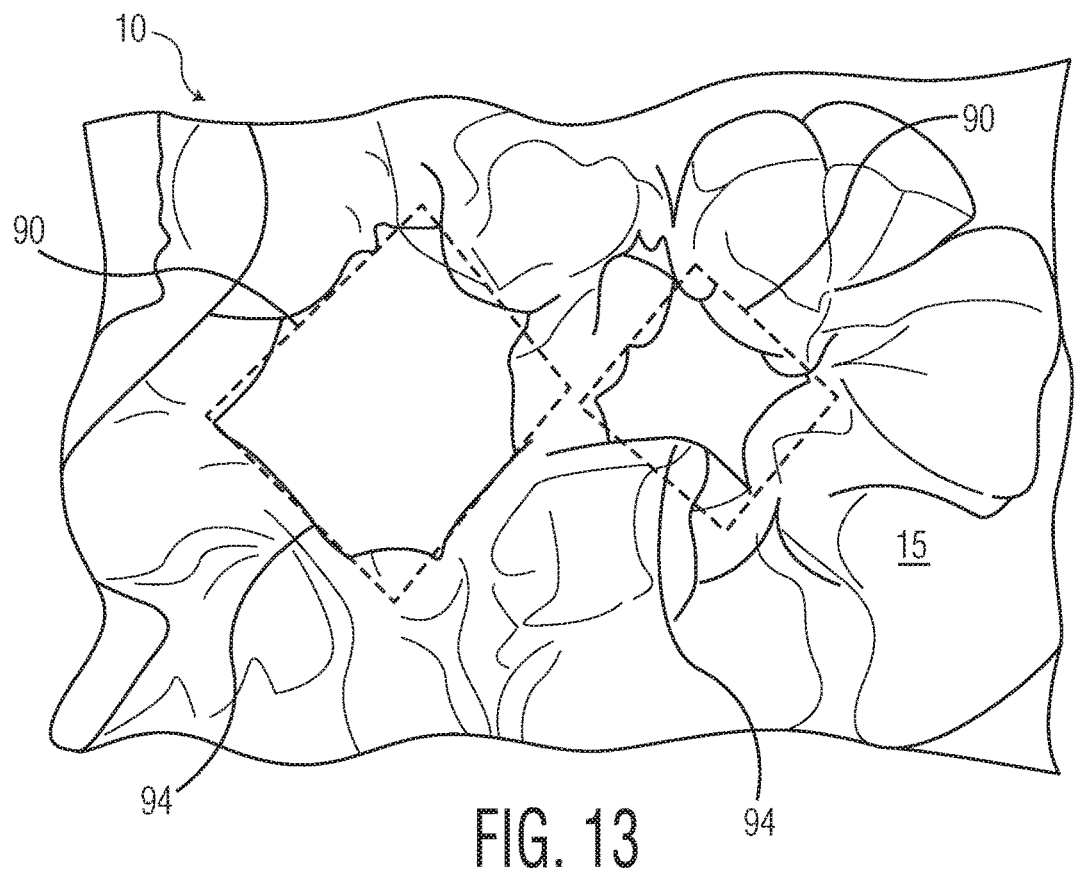
FIG. 13 is a plan schematic illustration of the prototype diaper portion of FIG. 12 with double-network polymer elements, after insult.
Figure 14:
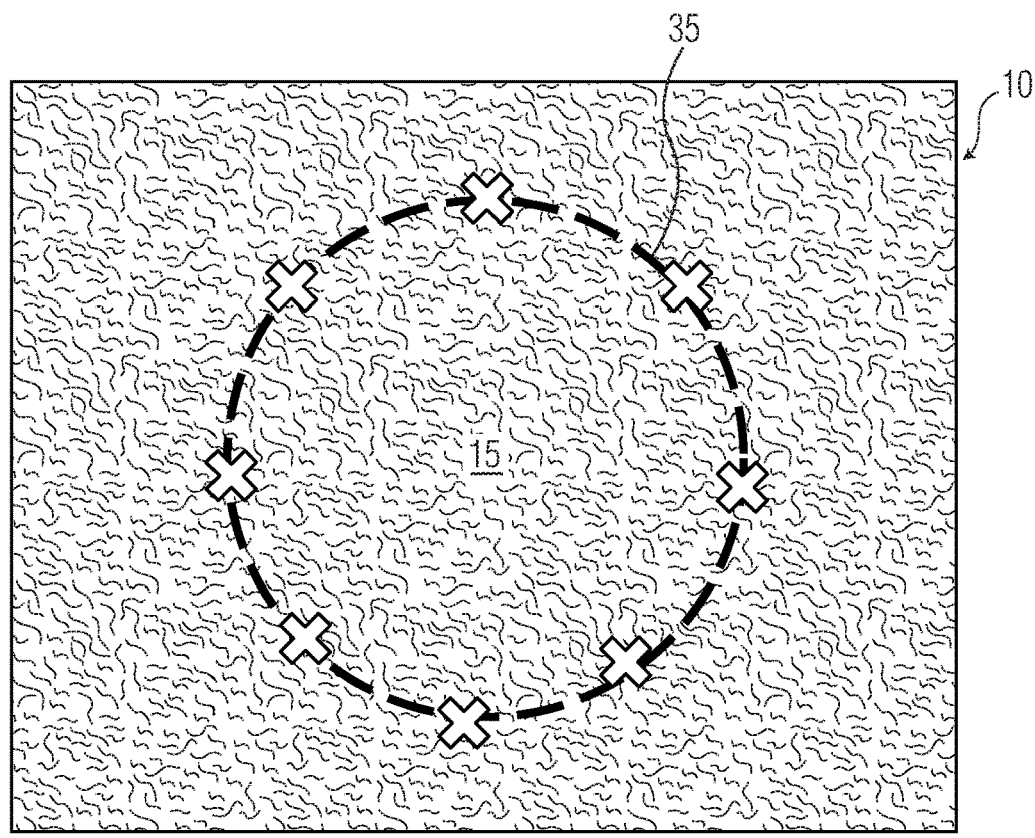
FIG. 14 is a plan schematic illustration of a portion of a prototype diaper with double-network polymer elements of the present disclosure, prior to insult.
Figure 15:
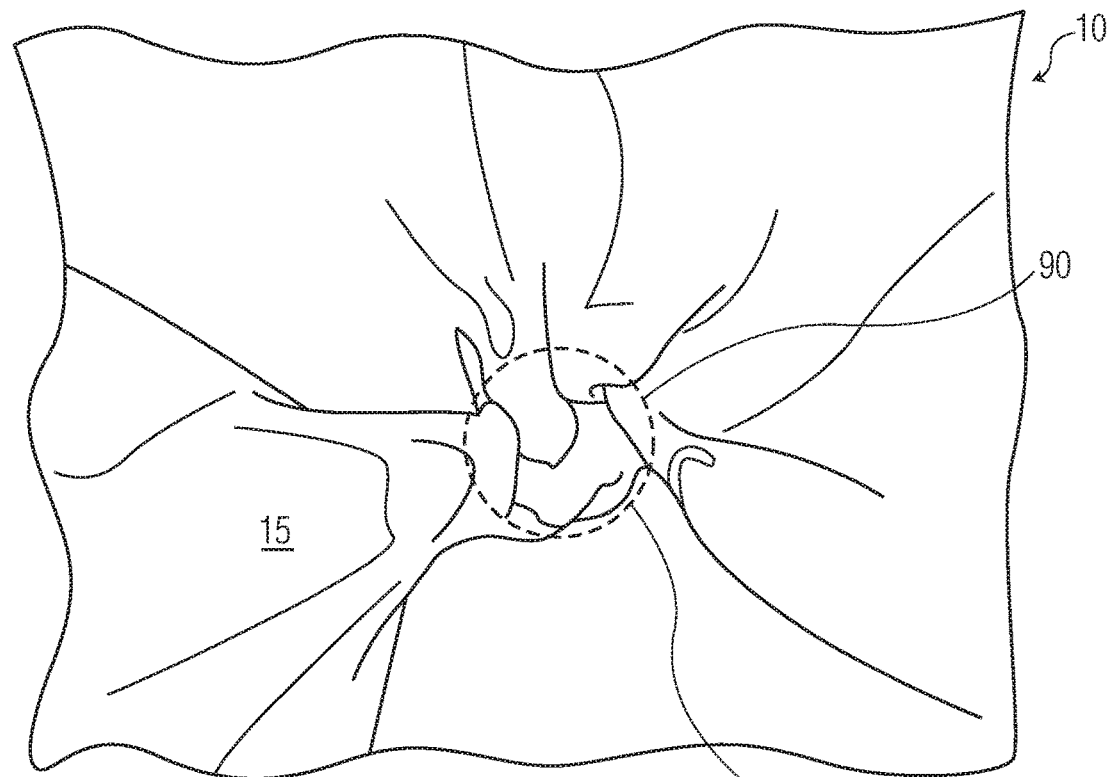
FIG. 15 is a plan schematic illustration of the prototype diaper portion of FIG. 14 with double-network polymer elements, after insult.

Double-network polymer elements can also be used in disposable absorbent products to create pockets upon insult, as illustrated in FIGS. 10-15. Liquid-triggered shrinkable double-network polymer elements 35 can be selectively placed between nonwovens (e.g., between a liner and another material) in the center of the chassis 15 of a diaper 10. Examples of such placement are illustrated in FIGS. 10, 12, and 14. In FIG. 10, the double-network polymer elements 35 are placed into the center of the chassis 15 as an X shape. In FIG. 12, the double-network polymer elements 35 are placed into the center of the chassis 15 as a window-pane pattern. In FIG. 14, the double-network polymer elements 35 are placed into the center of the chassis 15 as a circle. When the diapers 10 are insulted with saline as a urine simulant, the double-network polymer element fibers shrink, causing the formation of differently-shaped pockets 90. The X shape becomes the diamond/star-shaped pocket 92 illustrated in FIG. 11; the window pane pattern becomes the rectangular pockets 94 illustrated in FIG. 13; and the circle becomes the circular pocket 96 illustrated in FIG. 15. These pockets 90 can compartmentalize and hold fluid. The pockets 90 can also separate a bowel movement (BM) from urine, which can contribute to better skin health.

Figure 16:
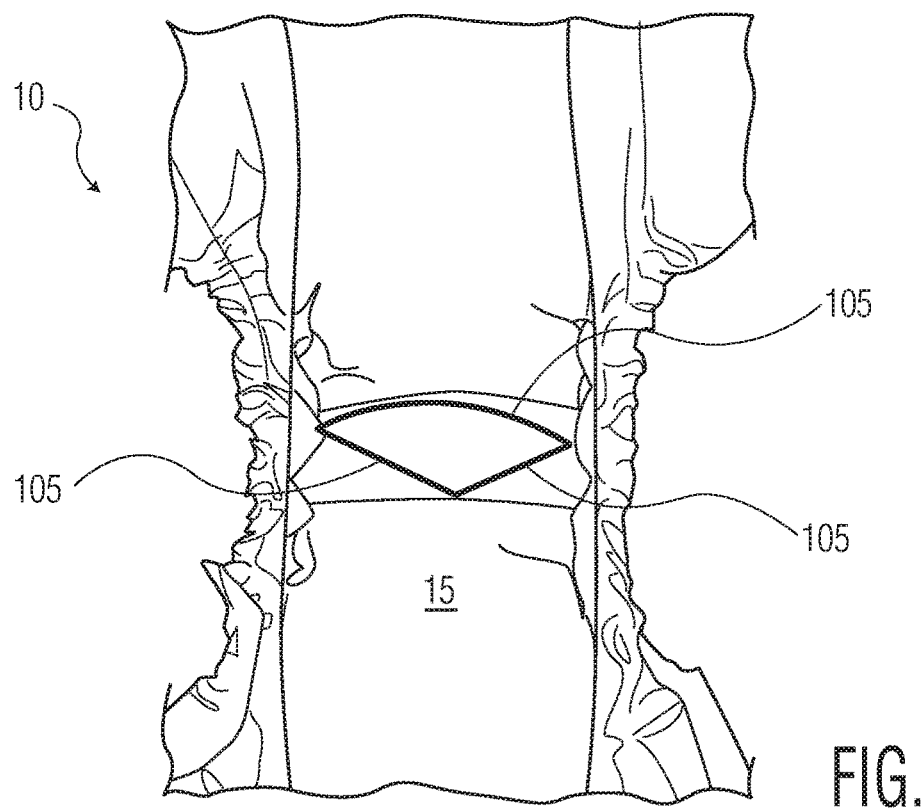
FIG. 16 is a plan schematic illustration of a prototype diaper with double-network polymer elements of the present disclosure, prior to insult.
Figure 17:
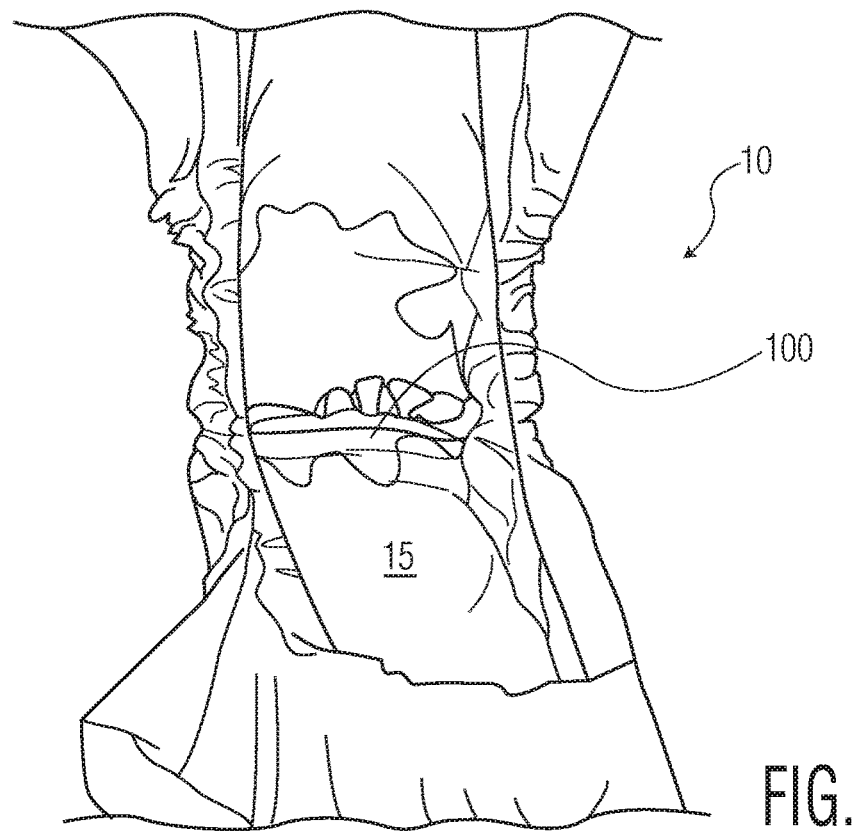
FIG. 17 is a plan schematic illustration of the prototype diaper of FIG. 16 with double-network polymer elements, after insult.
Figure 18:
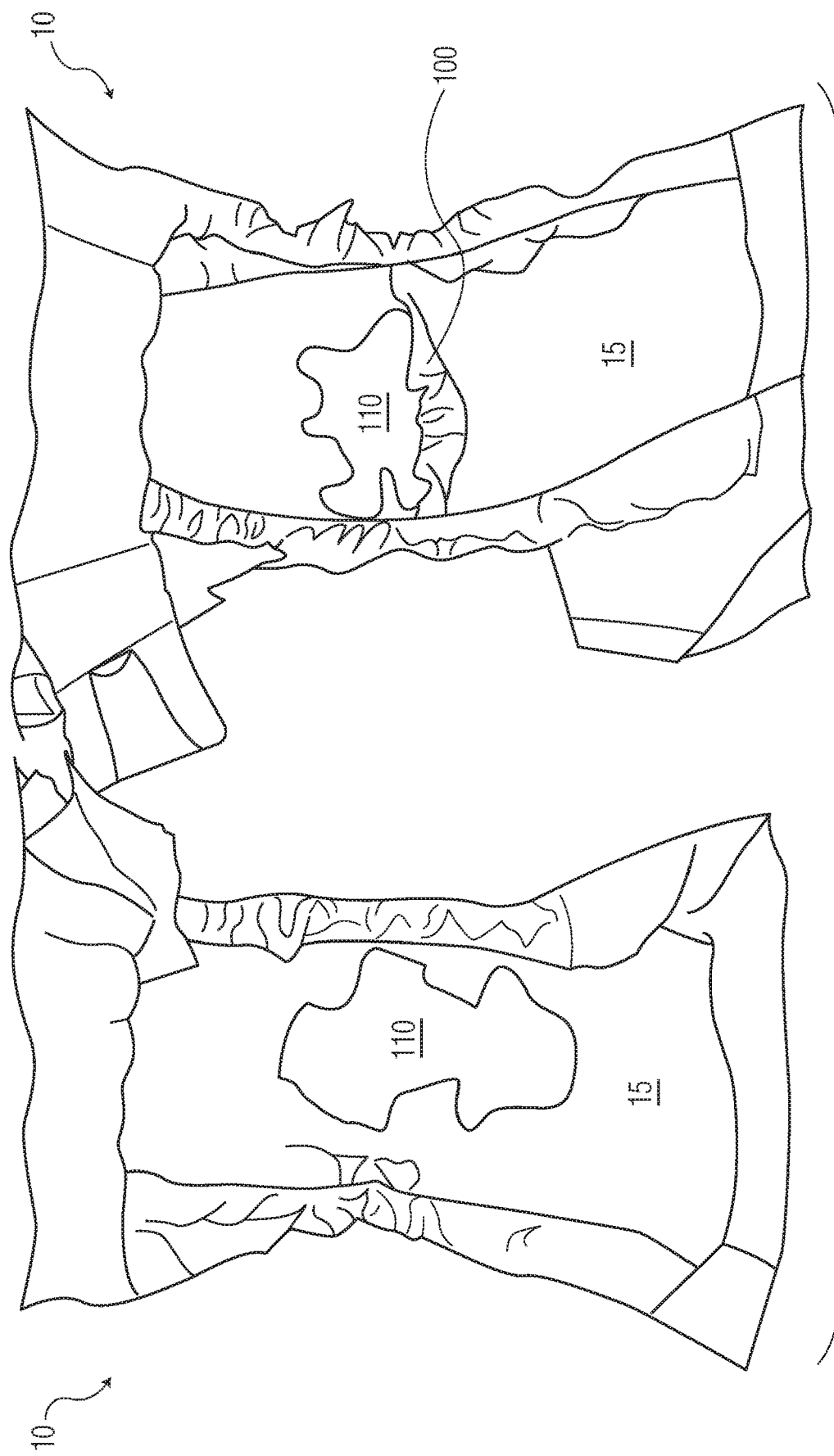
FIG. 18 is a plan schematic illustration of a control diaper (left) versus the prototype diaper of FIG. 16 (right), both after application of a bowel movement simulant.

Double-network polymer elements 105 can also be used in disposable absorbent products to create a urine-activated BM flap 100, as illustrated in FIGS. 16-18. Liquid-triggered shrinkable double-network polymer elements 105 can be selectively placed between nonwovens (e.g., between a liner and another material) in the center of the chassis 15 of a diaper 10. An example of such placement is illustrated in FIG. 16, where the double-network polymer elements 105 are placed into the center of the chassis 15 as a polygon, although any suitable shape can be used. When the diaper 10 is insulted with saline as a urine simulant, the double-network polymer element fibers shrink, creating a BM flap 100, as illustrated in FIGS. 17 and 18. This BM flap 100 is able to stop BM simulant 110 from flowing by containing the BM simulant 110 away from the front part of the diaper 10 and therefore away from the front part of the body, as illustrated in FIG. 18.

The aspects illustrated in FIGS. 1-18 are examples of various placements of double-network polymer elements. Other placements yielding other results after insult can be used as well. Different placements of the double-network polymer elements will result in different fit and containment performance. For example, the double-network polymer elements can be placed above or below a liner to enable shape change of product for better fit toward 3D body contour. Double-network polymer elements can be also used to create a dynamic flap that is activated on demand upon insult and controls free fluid until the fluid is fully absorbed by an absorbent layer or core.

In other aspects, a porous double-network polymer element can be used. Such a double-network polymer is highly porous because of its organic solvent treatment; the porosity allows for a fast fluid diffusion rate and therefore a fast shrinking kinetic. In still other aspects, the double-network polymer elements of the present disclosure exhibit a high and tunable shrink ratio. The double-network polymer elements of the present disclosure can shrink 70-80% when wetted. This level of shrinkage can be tailored by adjusting material composition and by post-synthesis treatment.

EXAMPLES

Examples demonstrating the preparation, use, and testing of various double-network polymer elements are presented in co-pending U.S. patent application Ser. Nos. 15/561,595 and 15/564,766, which are incorporated herein to the extent they do not conflict herewith. Those applications describe double-network hydrogel materials that are wet-triggered, shrink remarkably, and become elastic after hydrated.

Additional comparisons with conventional materials and advantageous properties of the double-network polymer elements are described below.

The double-network polymer elements described herein can provide the dimensional change benefits described herein without sacrificing the performance of conventional materials. One of these properties is the elastic properties of the double-network polymer elements after insult and shrink. Double-network polymer shrinkable fibers demonstrated good elasticity after wet, as shown in Table 1. The double-network polymer shrinkable fibers of the present disclosure are compared to commercially-available shrinkable fibers (such as SOLVRON yarn from Nitivy Co.) and to the elastics currently used commercially in HUGGIES brand diapers, LYCRA HYFIT elastic fibers from Invista. Double-network polymer shrinkable fibers of the present disclosure showed comparable strain at peak load with the commercial elastic fiber. When compared with a commercially available shrinkable fiber, the double-network polymer shrinkable fiber demonstrated better stretchability (higher strain at peak load) and lower hysteresis loss. The elastic properties of the double-network polymer shrinkable fibers after wet enable fit and comfort in disposable absorbent products.

TABLE 1

Comparison of Elasticity of Fibers After Wet

| Sample | Peak Load (gf) | Strain @ Peak Load % | Total Hysteresis % |
|---|---|---|---|
| Double-network polymer shrinkable fiber of the present disclosure, after wet | 83.7 | 576.0 | 56.2 |
| LYCRA HYFIT elastic fiber from Invista | 523.1 | 706.4 | 21.5 |
| Commercially-available shrinkable fiber | 412.6 | 268.4 | 77.3 |

In a first particular aspect, a disposable absorbent product includes a double-network polymer element including a cross-linked, covalently-bonded polymer and a reversible, partially ionicly-bonded polymer, wherein the element has a moisture level less than or equal to 15 percent of the total weight of the element, wherein the element comprises a latent retractive force, and wherein the element is configured to release the retractive force to achieve a dimensional change in the disposable absorbent product with exposure of the element to an aqueous liquid.

A second particular aspect includes the first particular aspect, wherein the element is porous.

A third particular aspect includes the first and/or second aspect, wherein the cross-linked, covalently-bonded polymer is polyacrylamide.

A fourth particular aspect includes one or more of aspects 1-3, wherein the reversible, partially ionicly-bonded polymer is sodium alginate.

A fifth particular aspect includes one or more of aspects 1-4, wherein the element is flexible and inelastic.

A sixth particular aspect includes one or more of aspects 1-5, wherein the release of the retractive force results in the element shrinking in at least one dimension and expanding in at least one dimension that is different from the shrinking dimension.

A seventh particular aspect includes one or more of aspects 1-6, wherein the disposable absorbent product is a diaper, training pant, feminine pad, feminine liner, or incontinence product.

An eighth particular aspect includes one or more of aspects 1-7, wherein the dimensional change is a flap movement.

A ninth particular aspect includes one or more of aspects 1-8, wherein the dimensional change is a curvature of the disposable absorbent product.

A tenth particular aspect includes one or more of aspects 1-9, wherein the dimensional change is a change in product topography.

An eleventh particular aspect includes one or more of aspects 1-10, wherein the element becomes elastic with exposure of the element to an aqueous liquid.

In a twelfth particular aspect, a disposable absorbent product includes a double-network polymer element including a cross-linked, covalently-bonded polymer and a reversible, partially ionicly-bonded polymer, wherein the element has a moisture level less than or equal to 15 percent of the total weight of the element, wherein the element comprises a latent retractive force, wherein the element is configured to release the retractive force to achieve a dimensional change in the disposable absorbent product with exposure of the element to an aqueous liquid, and wherein the release of the retractive force results in the element shrinking in at least one dimension and expanding in at least one dimension that is different from the shrinking dimension.

A thirteenth particular aspect includes the twelfth particular aspect, wherein the element is porous.

A fourteenth particular aspect includes the twelfth and/or thirteenth aspects, wherein the disposable absorbent product is a diaper, training pant, feminine pad, feminine liner, or incontinence product.

A fifteenth particular aspect includes one or more of aspects 12-14, wherein the element becomes elastic with exposure of the element to an aqueous liquid.

In a sixteenth particular aspect, a method for manufacturing a disposable absorbent product includes producing a double-network hydrogel including a cross-linked, covalently-bonded polymer and a reversible, ionicly-bonded polymer; elongating by force the double-network hydrogel in at least one direction; dehydrating while still elongated the double-network hydrogel to form a substantially-dehydrated double-network polymer element; releasing the force to produce the element, wherein elongating and dehydrating captures a latent retractive force in the element; and positioning the element in a disposable absorbent product such that a dimensional change in the disposable absorbent product is achieved with exposure of the element to an aqueous liquid.

A seventeenth particular aspect includes the sixteenth particular aspect, further comprising treating the double-network hydrogel with an organic solvent with a volatile and water-miscible organic solvent to replace a majority of water within the double-network hydrogel; wherein dehydrating includes evaporating the organic solvent while the double-network hydrogel is still elongated to form a substantially-dried double-network polymer system, and wherein the element is porous.

An eighteenth particular aspect includes the sixteenth and/or seventeenth aspects, wherein the element is configured to release the retractive force when exposed to liquid, and wherein the release of the retractive force results in the element shrinking in at least one dimension and expanding in at least one dimension that is different from the shrinking dimension.

A nineteenth particular aspect includes one or more of aspects 16-18, wherein the disposable absorbent product is a diaper, training pant, feminine pad, feminine liner, or incontinence product.

A twentieth particular aspect includes one or more of aspects 16-19, wherein the element becomes elastic with exposure of the element to an aqueous liquid.

While the disclosure has been described in detail with respect to the specific aspects thereof, it will be appreciated that those skilled in the art, upon attaining an understanding of the foregoing, can readily conceive of alterations to, variations of, and equivalents to these aspects. Accordingly, the scope of the present disclosure should be assessed as that of the appended claims and any equivalents thereto.

What is claimed is:

1. A disposable absorbent product comprising:
   a double-network polymer element including a cross-linked, covalently-bonded polymer and a reversible, partially ionicly-bonded polymer, wherein the element has a moisture level less than or equal to 15 percent of the total weight of the element, wherein the element is porous, wherein the element comprises a latent retractive force, and wherein the element is configured to release the retractive force to achieve a dimensional change in the disposable absorbent product with exposure of the element to an aqueous liquid, wherein the dimensional change is a flap movement or a curvature of the disposable absorbent product.

2. The disposable absorbent product of claim 1, wherein the cross-linked, covalently-bonded polymer is polyacrylamide.

3. The disposable absorbent product of claim 1, wherein the reversible, partially ionicly-bonded polymer is sodium alginate.

4. The disposable absorbent product of claim 1, wherein the element is flexible and inelastic.

5. The disposable absorbent product of claim 1, wherein the release of the retractive force results in the element shrinking in at least one dimension and expanding in at least one dimension that is different from the shrinking dimension.

6. The disposable absorbent product of claim 1, wherein the disposable absorbent product is a diaper, training pant, feminine pad, feminine liner, or incontinence product.

7. The disposable absorbent product of claim 1, wherein the dimensional change is a flap movement.

8. The disposable absorbent product of claim 1, wherein the dimensional change is a curvature of the disposable absorbent product.

9. The disposable absorbent product of claim 1, wherein the element becomes elastic with exposure of the element to an aqueous liquid.

10. A disposable absorbent product comprising:
    a double-network polymer element including a cross-linked, covalently-bonded polymer and a reversible, partially ionicly-bonded polymer, wherein the element has a moisture level less than or equal to 15 percent of the total weight of the element, wherein the element is porous, wherein the element comprises a latent retractive force, wherein the element is configured to release the retractive force to achieve a dimensional change in the disposable absorbent product with exposure of the element to an aqueous liquid, wherein the dimensional change is a flap movement or a curvature of the disposable absorbent product and wherein the release of the retractive force results in the element shrinking in at least one dimension and expanding in at least one dimension that is different from the shrinking dimension.

11. The disposable absorbent product of claim 10, wherein the disposable absorbent product is a diaper, training pant, feminine pad, feminine liner, or incontinence product.

12. The disposable absorbent product of claim 10, wherein the element becomes elastic with exposure of the element to an aqueous liquid.

13. A method for manufacturing a disposable absorbent product, the method comprising:
    producing a double-network hydrogel including a cross-linked, covalently-bonded polymer and a reversible, ionicly-bonded polymer;
    elongating by force the double-network hydrogel in at least one direction;
    dehydrating while still elongated the double-network hydrogel to form a substantially-dehydrated double-network polymer element;
    releasing the force to produce the element, wherein elongating and dehydrating captures a latent retractive force in the element; and
    positioning the element in a disposable absorbent product such that a dimensional change in the disposable absorbent product is achieved with exposure of the element to an aqueous liquid, wherein the dimensional change is a flap movement or a curvature of the disposable absorbent product.

14. The method of claim 13, further comprising treating the double-network hydrogel with an organic solvent with a volatile and water-miscible organic solvent to replace a majority of water within the double-network hydrogel; wherein dehydrating includes evaporating the organic solvent while the double-network hydrogel is still elongated to form a substantially-dried double-network polymer system, and wherein the element is porous.

15. The method of claim 13, wherein the element is configured to release the retractive force when exposed to liquid, and wherein the release of the retractive force results in the element shrinking in at least one dimension and expanding in at least one dimension that is different from the shrinking dimension.

16. The method of claim 13, wherein the disposable absorbent product is a diaper, training pant, feminine pad, feminine liner, or incontinence product.

17. The method of claim 13, wherein the element becomes elastic with exposure of the element to an aqueous liquid.

* * * * *